US00PP26610P3

(12) United States Plant Patent
Slaughter et al.

(10) Patent No.: US PP26,610 P3
(45) Date of Patent: Apr. 19, 2016

(54) NECTARINE TREE 'BURNECTTWENTYEIGHT'

(50) Latin Name: ***Prunus persica* (subspecies *nucipersica*)**
Varietal Denomination: Burnecttwentyeight

(71) Applicants: John K. Slaughter, Fresno, CA (US); Timothy J. Gerdts, Kingsburg, CA (US)

(72) Inventors: John K. Slaughter, Fresno, CA (US); Timothy J. Gerdts, Kingsburg, CA (US)

(73) Assignee: THE BURCHELL NURSERY, INC., Oakdale, CA (US)

( * ) Notice: Subject to any disclaimer, the term of this patent is extended or adjusted under 35 U.S.C. 154(b) by 156 days.

(21) Appl. No.: 13/998,894

(22) Filed: Dec. 19, 2013

(65) Prior Publication Data

US 2015/0181781 P1 Jun. 25, 2015

(51) Int. Cl.
*A01H 5/08* (2006.01)

(52) U.S. Cl.
USPC ..... Plt./190

(58) Field of Classification Search
USPC ..... Plt./190
See application file for complete search history.

*Primary Examiner* — Keith Robinson
(74) *Attorney, Agent, or Firm* — Randall Danskin

(57) ABSTRACT

A new and distinct variety of nectarine tree which is denominated varietally as 'Bunecttwentyeight' is described, and which further produces an attractively colored, firm-fleshed, clingstone nectarine, which is mature for harvesting and shipment approximately June 16 to June 27 under the ecological conditions prevailing in the San Joaquin Valley of central California.

1 Drawing Sheet

Botanical designation: The present invention relates to a new, novel and distinct variety of nectarine tree, *Prunus persica* (subspecies *nucipersica*).

Varietal denomination: 'Burnecttwentyeight.'

BACKGROUND OF THE NEW VARIETY

The present variety of nectarine tree resulted from an ongoing program of fruit and nut tree breeding. The purpose of this program is to improve the commercial quality of available deciduous fruit and nut varieties, and rootstocks, by creating and releasing promising selections of *Prunus, Malus Punica* and *Regia* species. To this end we make both controlled and hybrid cross pollinations each year in order to produce seedling populations from which improved progenies are evaluated and selected.

The seedling 'Burnecttwentyeight' was originated by us from a population of seedlings grown in our experimental orchards which are located near Fowler, Calif. The seedlings, grown on their own roots, were the result of a controlled cross made in February of 2007, of the yellow-fleshed nectarine tree, 'Burnecttwentytwo' (U.S. Plant Pat. No. 21,724), which was the seed parent; and the white-fleshed saucer peach tree 'Galaxy' (non-patented) and, which was used as the pollen parent. One seedling, N32.123, which is the present variety, exhibited especially desirable characteristics, and was marked for subsequent observation. After the 2009 fruiting season, the new, present variety, was selected for advanced evaluation, and propagation.

ASEXUAL REPRODUCTION

Asexual reproduction of this new and distinct variety of nectarine tree was accomplished by budding the new nectarine tree to 'Nemaguard' Rootstock (non-patented). This was performed by us in our experimental orchard which is located near Fowler, Calif. Subsequent evaluations have shown that these asexual reproductions run true to the original tree. All characteristics of the original tree, and its fruit, were established, and appear to be transmitted through succeeding asexual propagations. We have observed fruit from approximately 15 propagated trees for the past 4 successive years.

SUMMARY OF THE VARIETY

'Burnecttwentyeight' is a new and distinct variety of nectarine tree, which is considered of large size, and which has vigorous growth. This new nectarine tree variety is also a regular and productive bearer of relatively large, firm, acidic, yellow fleshed, non-melting, clingstone fruit which have good flavor and eating quality. The tree of the present variety displays a medium chilling requirement of approximately 450 hours. Still further, the present tree also produces relatively uniformly sized fruit throughout the tree. Additionally, the fruit produced by the present tree has a very high degree of red skin coloration, a firm flesh, and also appears to have good handling and shipping qualities. The 'Burnecttwentyeight' Nectarine tree bears fruit which are ripe for commercial harvesting and shipment on approximately June 16 to June 26 under the ecological conditions prevailing in the San Joaquin Valley of central California. In relative comparison to the seed parent, 'Burnecttwentytwo' (U.S. Plant Pat. No. 21,724), the 'Burnecttwentyeight' nectarine ripens 10-14 days later. In relative comparison to the pollen parent, the 'Galaxy' peach tree, the current variety produces a nectarine which has a globose form. The nectarine tree, 'Spring Bright' (U.S. Plant Pat. No. 7,507), which is the most closely similar commercial variety known at this time produces fruit which are both smaller and further has less external red blush than what is displayed by the present new variety. Additionally, the current variety displays a more consistent fruit set from which to select fruiting positions, and fruit numbers per tree.

BRIEF DESCRIPTION OF THE DRAWINGS

The accompanying drawing which is provided is a color photograph of two whole mature fruit taken in their $5^{th}$ year, and displaying both the apical and basal aspects thereof. This reveals the flesh and the stone characteristics of the present variety. The external coloration of the fruit, as shown, is sufficiently matured for harvesting and shipment. Additionally, the photograph displays a sample vegetative shoot bearing typical leaves, and a typical stone, with the flesh removed. The colors in the photograph are as nearly true as is reasonably possible in a color representation of this type. Due to chemical development, processing, and printing, the leaves and fruit depicted in these photographs may or may not be accurate when compared to the actual specimen. For this reason, future color references should be made to the color plates (Royal Horticultural Society Fourth Edition, 2001.) and the descriptions provided, hereinafter.

NOT A COMMERCIAL WARRANTY

The following detailed description has been prepared to solely comply with the provisions of 35 U.S.C. §112, and does not constitute a commercial warranty, (either expressed or implied), that the present variety will, in the future, display the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological details of this new and distinct variety of nectarine tree, the following has been observed during the sixth fruiting season under the ecological conditions prevailing at our orchards which are located near the town of Fowler, county of Fresno, state of Calif. All major color code designations are by reference to The R.H.S. Color Chart (Fourth Edition, 2001) and which is provided by The Royal Horticultural Society of Great Britain. Common color names are also occasionally used.

TREE

Size:

*Generally*.—Considered medium-large as compared to other common commercial nectarine cultivars ripening in the same season of maturity.

Tree height: The tree of the present variety was pruned to a height of approximately 305.0 cm to about 310.0 cm at maturity. There exists ample tree vigor to extend the tree height beyond the stated range, and which is typically established by individual fruit growers.

Canopy width: The canopy width of the present variety was pruned to occupy a width of approximately 300.0 cm to 310.0 cm at maturity. As noted above, there exists ample tree vigor to extend the tree canopy width beyond the stated range and which is typically established by individual fruit growers.

Vigor: Considered vigorous. The present variety grew from about 190.0 cm to 205.0 cm in height during the first growing season. The new nectarine tree variety was pruned to a height of approximately 150.0 cm during the first dormant season, and primary scaffolds were then selected for the desired and resulting tree structure.

Productivity: Productive. The fruit set varies from 4.0 to several times more than the desired crop load. The fruit set is spaced by thinning to develop the remaining fruit into the desired market-sized fruit. The number of the fruit set varies with the prevailing climatic conditions, and the current cultural practices employed during the bloom period.

Fruit bearing: Regular. Fruit set has been heavy, and significant thinning was necessary during the past 4 growing seasons.

Tree form: Upright, and pruned into a resulting vase shape.

Tree density: Considered medium dense. It has been discovered that pruning the branches from the center of the tree to obtain a resulting vase shape allows for a proper amount of air movement in the tree, and an appropriate amount of sunlight to reach the tree so as to enhance the resulting fruit color and further encourage the renewal of fruiting wood throughout the entire tree.

Hardiness: The present tree was grown, and evaluated in USDA Hardiness Zone 9.

Winter chilling requirements: The winter chilling requirements of the new tree are approximately 450 hours at a temperature below 7.0 degrees C. The present variety appears to be hardy under typical Central San Joaquin Valley climatic conditions.

Rooting habit: Not available. The present variety is grown on commercial root stock so this information is not relevant to the description of the new variety.

Root color: Inasmuch as the present variety is grown on commercial root stock this information is not available.

Time to initiate roots and provide a rooted plant: This information is not available. The present variety is grown on commercial root stock.

TRUNK

Diameter: Approximately 17.0 cm in diameter when measured at a distance of approximately 15.24 cm above the soil level. This was measured on trees at the end of the fourth growing season.

Bark texture: Considered moderately rough, with numerous folds of papery scarfskin being present.

Lenticels: Numerous flat, oval lenticels are present. The lenticels range in size from approximately 4.0 to about 6.0 millimeters in width; and from about 1.0 to about 2.0 millimeters in height. It should be noted that as the bark of the trees mature, the lenticels become less apparent, and also less abundant.

Lenticel color: Considered an Orange-Brown, (RHS Greyed-Orange Group 166 D).

Bark coloration: Variable, but it is generally considered to be Gray-Brown, (RHS Greyed-Orange Group 174 A).

BRANCHES

Size: Considered medium-large for the variety.

Diameter: Average as compared to other nectarine tree varieties. The branches have a diameter of about 9.0 centimeters when measured on trees during the fourth year after grafting. Flowering shoot thickness—Average.

Surface texture: Average, and appearing furrowed on wood which is several years old.

Crotch angles: Primary branches are considered variable between about 50 to about 52 degrees when measured from the horizontal axis. This particular characteristic varies due to the influence of variable ecological conditions and cultural practices, however.

Current season shoots: Surface texture—Substantially glabrous.

Internode length: Approximately 2.4 to about 2.7 cm. This tree characteristic is highly dependent upon plant vigor and is further influenced by nutrition, soil quality, pruning and tree care.

Color of mature branches: Medium-brown, (RHS Greyed-Orange 166 B).

Current season shoots:

*Color*.—Light green, (RHS Green Group 137 B). The color of the new shoot tips is considered a bright and shiny green (RHS Green Group 137 A).

LEAVES

Size: Considered medium for the species. Leaf measurements have been taken from vigorous, upright, current-season growth, at approximately mid-shoot.

Leaf length: Approximately 148.0 to about 155.0 millimeters.

Leaf width: Approximately 34.0 to about 37.0 millimeters.

Leaf base shape: Slightly oblique relative to the longitudinal axis of the leaf.

Leaf form: Lancelolate.

Leaf tip form: Considered rostratus.

Leaf color:

*Upper surface*.—Dark green, (approximately RHS Green Group 136 A).

Leaf texture: Both upper and lower leaf surfaces are glabrous.

Leaf color:

*Lower surface*.—Medium green, (RHS Green Group 137 B).

Leaf venation: Pinnately veined.

Mid-vein:

*Color*.—Light yellow green, (RHS Yellow-Green Group 144 B).

Leaf margins:

*Generally*.—Slightly undulating.

*Form*.—Considered crenate, occasionally doubly crenate.

*Uniformity*.—Considered generally uniform.

Leaf petioles:

*Size*.—Considered long.

*Length*.—About 13.0 to about 14.0 mm.

*Diameter*.—About 1.5 to about 2.0 mm.

*Color*.—Pale green, (RHS Yellow-Green Group 150D).

*Leaf petiole strength*.—Durable for the species until senescence.

*Surface texture*.—Glabrous.

Leaf glands:

*Size*.—Considered generally small. About 1.0 mm in height, and about 1.0 mm in width.

*Number*.—Generally one per side, occasionally two per side may be found. Rarely it appears that glands are absent.

*Type*.—Globose. Considered reasonably unappressed relative to the petiole margin, and relatively small. The glands on more mature leaves are occasionally senescent.

*Color*.—Orange brown, (RHS Greyed-Green Group N189 B).

Leaf stipules:

*Size*.—Medium.

*Length*.—Approximately 5.0-7.0 mm.

*Width*.—Approximately 1.0-1.5 mm.

*Number*.—Typically 2 per leaf bud, and up to 6 per shoot tip.

*Form*.—Lanceolate in form, and having a serrated margin.

*Color*.—Green, (RHS Green Group 141 A) when juvenile, but then graduating to a brown color, (RHS Greyed-Orange Group 177 B) with advancing senescence. The stipules are considered to be early deciduous.

FLOWER BUDS

Flower buds:

*Generally*.—The floral buds, depending upon the stage of development, are approximately 8.0 millimeters wide; and about 12.0 millimeters long; conic in form; and slightly appressed relative to the bearing shoot.

*Flower bud density*.—Very dense.

Flower bud scales:

*Color*.—The bud scales are reddish-brown, (approximately RHS Greyed-Red Group 178 A). The buds are considered hardy under typical central San Joaquin Valley climatic conditions.

Hardiness: No winter injury has been noted during the last several years of evaluation in the central San Joaquin Valley. The current variety has not been intentionally subjected to drought or heat stress, and therefore this information is not presently available. The current variety is considered to be a lower chilling requirement variety for the region where it is currently grown. It is possible for this new variety to experience frost damage on either the developing flowers or small fruit due to the early initiation of the blooming period, and further exposure of the new flowers or developing fruit to the damaging effects of tow temperatures which are sometimes experienced during the late winter months, and after the first bloom.

FLOWERS

Blooming time: Considered early to mid-season in relative comparison to other commercial nectarine cultivars grown in the central San Joaquin Valley.

Date the first bloom was observed: Feb. 17, 2013. Date of full bloom was first observed on Feb. 24, 2013. The date of bloom varies slightly with the prevailing climatic conditions, and cultural practices which are employed.

Duration of the bloom: Approximately 7-10 days. This characteristic varies slightly with the prevailing climatic conditions.

Flower class: Perfect and perigynous.

Flower type: The variety is considered to have a showy-type flower.

Flower size: The flower diameter at full bloom is approximately 38.0 to about 42.0 millimeters.

Bloom quantity: Considered very abundant, and dense.

Flower bud frequency: Normally 2 flower buds appear per node. Rarely 3 buds per node may be observed.

Petal size:

*Generally*.—Considered medium-large for the species.

*Length*.—Approximately 18.0 to about 20.0 millimeters.

*Width*.—Approximately 16.0 to about 18.0 millimeters.

Petal form: Rotund to slightly ovate.
Petal count: Typically 5. Occasionally individual flower petal counts are doubled.
Petal texture: Both the upper and lower surfaces are glabrous.
Petal color: Considered Light pink, (RHS Red-Purple Group 62 B) to a medium pink, (RHS Red-Purple Group N57 C).
Fragrance: Slight.
Petal claw:
*Form.*—The claw is considered truncate in shape, and has a generally large size when compared to other varieties.
*Length.*—Approximately 11.0 to about 13.0 millimeters.
*Width.*—Approximately 10.0 to about 11.0 millimeters.
Petal margin shapes: Generally considered variable, from nearly smooth, to moderately undulate.
Petal apex:
*Generally.*—The petal apices appear entire without an apical groove.
Flower pedicel:
*Length.*—Considered medium-long, and having an average length of approximately 5.0 to about 7.0 millimeters.
*Diameter.*—Considered average, approximately 2.0 to 3.0 millimeters.
*Color.*—A pale green when the bud scales are removed, (RHS Greyed-Green Group 194 B).
*Strength.*—Moderately delicate.
*Surface texture.*—Glabrous.
Floral nectaries:
*Color.*—An orange-brown, (RHS Greyed-Orange Group N172 B).
Calyx:
*Surface texture.*—Generally glabrous.
*Color.*—A dull red, (approximately RHS Greyed-Orange Group 176 A).
Sepals:
*Surface texture.*—The upper surface has a short, fine, pubescent texture. The lower surface is considered glabrous.
*Number.*—Nearly always 5.
*Size.*—Average; and ovate in form.
*Sepal length.*—Approximately 5.0-6.0 mm.
*Sepal width.*—Approximately 4.0-6.0 mm.
*Sepal margin.*—Entire.
*Sepal color.*—A dark reddish purple, (approximately RHS Greyed-Red Group 176 B).
Anthers:
*Generally.*—Large in size.
*Color.*—Red to reddish-purple, (approximately RHS Greyed-Purple Group 187 C) prior to dehiscence.
Pollen production: Pollen is abundant, and has a yellow color, (approximately RHS Yellow Group 11 A).
Fertility: Self Fertile.
Filaments:
*Size.*—Variable in length, approximately 13.0 to about 17.0 millimeters in length.
*Color.*—Considered a pale pink, (RHS Red-Purple Group 65 C) at maturity. At flower maturity the stamens grow to be superior to the petals.
Pistil:
*Number.*—Normally 1, very rarely 2.
*Size.*—Average.
*Length.*—Approximately 16.0 to about 20.0 millimeters including the ovary.
*Color.*—Considered a very pale green, (approximately RHS Yellow-Green Group 145 C).
*Surface texture.*—The variety has a long glabrous pistil. Generally the stigma is superior to the anthers by approximately 10-20 mm.

FRUIT

Maturity when described: Firm ripe condition (shipping ripe).
*Date of first picking.*—Approximately Jun. 16, 2013.
*Date of last picking.*—Jun. 27, 2013. The date of harvest varies slightly with the prevailing climatic conditions.
Size:
*Generally.*—Considered large, and uniform.
Average cheek diameter: Approximately 72.0 to about 77.0 millimeters.
Average axial diameter: Approximately 72.0 to about 76.0 millimeters.
Typical weight: Approximately 258.0 grams. This characteristic is highly dependent upon the prevailing cultural practices. A mucron tip at the pistil end of the fruit is absent.
Fruit form:
*Generally.*—Rounded to slightly oblate. The fruit is generally uniform in symmetry.
Fruit acidity: This information is not available.
Fruit suture: Shallow, and extending from the mid-equatorial region to the apex. No apparent callousing or stitching exists along the suture line.
Suture:
*Color.*—The background color appears to be an orange yellow, (approximately RHS Orange Group N25 D), with occasional red coloration, (approximately RHS Red Group 46 A).
Ventral surface:
*Form.*—Full. The fruit can exhibit some lobbing on one side of the suture.
Apex:
*Shape.*—Rounded.
Base:
*Shape.*—Retuse.
Stem cavity:
*Shape.*—Rounded and relatively shallow. The average depth of the stem cavity is about 1.0 cm. The average width of the stem cavity is about 1.90 cm.
Fruit skin:
*Thickness.*—Considered medium in thickness, and tenacious to the flesh.
*Surface texture.*—Glabrous.
*Taste.*—Slight astringency is noted.
*Tendency to crack.*—Cracking has not been observed. Russeting has not been observed to date on the oldest bearing trees.
Fruit skin color:
*Blush color.*—The blush color is variable from a medium red, (approximately RHS Red Group 44 A) to a dark red, (approximately RHS Red Group 46 A). The blush color ranges from approximately 85% to about 95% of the fruit surface depending upon the sunlight exposure and the prevailing growing conditions.
Ground color: Generally a deep yellow, (approximately RHS Orange Group 15 D).
Fruit glossiness: Medium to strong.

Fruit stem: Moderate in length, approximately 7.0 to about 9.0 millimeters.

*Diameter.*—Approximately 2.0 to about 3.0 millimeters.

*Color.*—Light tan, (approximately RHS Greyed-Orange Group 164 D).

Flesh:

*Ripening.*—Evenly.

*Texture.*—Firm, and dense. Considered non-melting.

*Fibers.*—Few, small, and tender ones are apparent.

*Aroma.*—Slight.

*Eating quality.*—Considered good.

*Flavor.*—Considered sweet and acidic. The flavor is considered pleasant.

*Acid.*—Considered an acidic fruit. Approximately 0.80 titratable acidity was detected. Flesh acidity varies slightly with growing conditions and flesh maturity.

*Juice production.*—Moderate.

*Brix.*—About 14.5 degrees. This characteristic varies slightly with the number of fruit per tree, the prevailing cultural practices, and the surrounding climatic conditions.

*Flesh color.*—Yellow, (approximately RHS Yellow-Orange Group 17 C).

STONE

Type: Clingstone.

Size: Considered medium-large for the variety. The stone size varies with the resulting crop load, and tree vigor.

Length: Average, about 27.0 to about 31.0 millimeters.

Width: Average, about 22.0 to about 25.0 millimeters.

Diameter: Average, about 17.0 to about 23.0 millimeters.

Stone form: Obovoid.

Stone base: The stone is relatively uniform in its margin relative to the stone's vertical axis.

Apex:

*Shape.*—The stone apex is relatively smooth.

Stone surface:

*Surface texture.*—Substantial pitting is evident and in general is seen from the base, and extending past the equatorial plane. Grooving is usually observed along the pit margin, and near the tip as well as on the ventral side.

*Ridges.*—Texture — The surface texture is generally rounded.

*Ventral edge.*—Width — Considered medium, and having a dimension of approximately 3.0 to about 4.0 millimeters when this dimension is measured at mid-suture.

*Dorsal edge.*—Shape — Full, moderately grooved, and having relatively smooth edges.

Stone color: The color of the dry stone is a tan (approximately RHS Greyed-Orange Group 172 B).

Tendency to split: On rare occasions splits have been noted.

Kernel:

*Generally.*—The kernel, when the fruit is picking ripe, is not completely mature as compared to the kernels of fruit varieties having a greater developmental period.

*Length.*—Approximately 18.0-121.0 mm.

*Width.*—Approximately 14.0-18.0 mm.

*Thickness.*—Approximately 3.0-6.0 mm.

*Form.*—Considered ovoid.

*Surface texture of the kernel.*—Pubescent.

*Color.*—Considered to be a pale tan (RHS Greyed-Yellow Group 162 D).

Use: The new variety 'Burnecttwentyeight' is considered to be a Nectarine tree which matures early in the season, and which produces fruit, which are considered firm, attractively colored, flavorful, and which are useful for both local and long distance shipping.

Keeping quality: Appears excellent. The fruit has stored well for up to 25 days after harvest at 1.0 degree Celsius.

Shipping quality: Good. The fruit of the new nectarine tree variety showed minimal bruising of the flesh, or skin damage, after being subjected to normal harvest and packing procedures.

Resistance to insects and disease: No particular susceptibilities were noted. The present variety has not been tested to expose or detect any susceptibilities or resistances to any known plant and/or fruit diseases. No tests have been conducted or planned subsequent to the filing of the present plant patent application.

Although the new variety of nectarine tree possesses the described characteristics when grown under the ecological conditions prevailing near Fowler, Calif., in the central part of the San Joaquin Valley of California, it should be understood that variations of the usual magnitude and characteristics incident to changes in growing conditions, fertilization, pruning, pest control and horticultural management are to be expected.

Having thus described and illustrated our new variety nectarine tree, what we claim is new and desire to secure by Plant Letters Patent is:

1. A new distinct variety of nectarine tree, substantially as illustrated and described, and which is characterized principally as to novelty by producing an attractively colored, non-melting, yellow-fleshed, acidic flavored clingstone nectarine which is mature for harvesting and shipment approximately June 16 to June 27 under the ecological conditions prevailing in the San Joaquin Valley of central California.

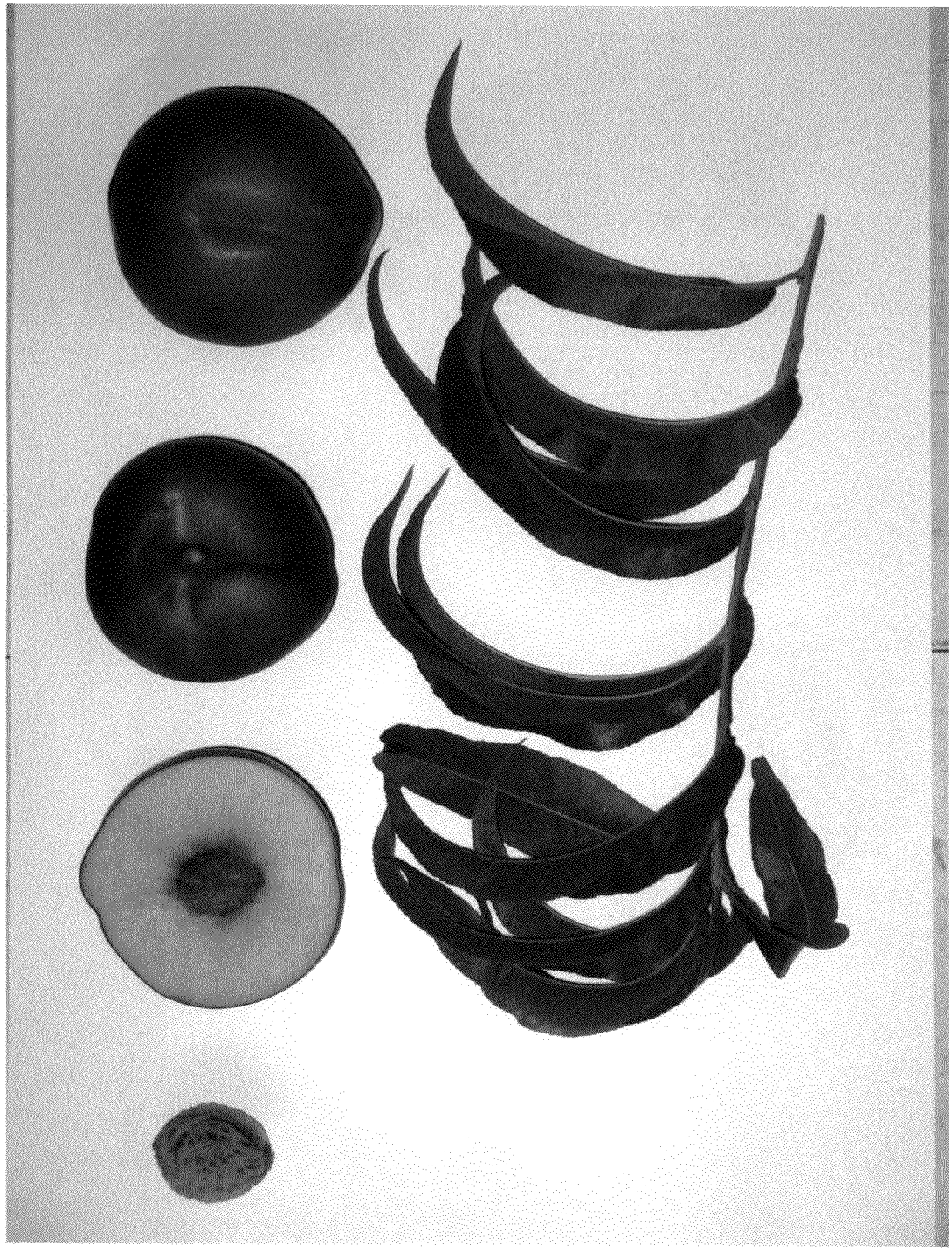

* * * * *